US009144461B2

(12) United States Patent
Kruecker et al.

(10) Patent No.: US 9,144,461 B2
(45) Date of Patent: Sep. 29, 2015

(54) FEEDBACK SYSTEM FOR INTEGRATING INTERVENTIONAL PLANNING AND NAVIGATION

(75) Inventors: Jochen Kruecker, Washington, DC (US); Sandeep Dalal, Cortlandt Manor, NY (US); Sheng Xu, Rockville, MD (US); Bradford J. Wood, Potomac, MD (US)

(73) Assignees: Koninklijke Philips N.V., Eindhoven (NL); THE UNITED STATES OF AMERICA, as represented by the Secretary, Department of Health and Human Services, Washington, DC (US)

( * ) Notice: Subject to any disclaimer, the term of this patent is extended or adjusted under 35 U.S.C. 154(b) by 1040 days.

(21) Appl. No.: 13/131,886
(22) PCT Filed: Nov. 5, 2009
(86) PCT No.: PCT/IB2009/054923
§ 371 (c)(1),
(2), (4) Date: May 31, 2011
(87) PCT Pub. No.: WO2010/064154
PCT Pub. Date: Jun. 10, 2010

(65) Prior Publication Data
US 2011/0251607 A1  Oct. 13, 2011

Related U.S. Application Data

(60) Provisional application No. 61/119,464, filed on Dec. 3, 2008.

(51) Int. Cl.
*A61B 18/14* (2006.01)
*A61B 18/18* (2006.01)
(Continued)

(52) U.S. Cl.
CPC ............ *A61B 18/18* (2013.01); *A61B 18/1206* (2013.01); *A61B 18/1815* (2013.01);
(Continued)

(58) Field of Classification Search
USPC .......... 606/32–34, 45–50; 607/101, 102, 122; 600/424–429
See application file for complete search history.

(56) References Cited

U.S. PATENT DOCUMENTS 5,485,839 A  1/1996  Aida
5,553,618 A  9/1996  Suzuki
(Continued)

FOREIGN PATENT DOCUMENTS

EP    1504713 A1   2/2005
WO    2007129308 A2   11/2007
WO    2008030263 A1   3/2008

OTHER PUBLICATIONS

By B. Wood et al. "Technologies for Guidance of Readiofrequency Ablation in the Multimodality Interventional Suite of the Future" Journal of Vascular and Interventional Radiology, VA, vol. 18, No. 1, Jan. 19, 2007, pp. 9-24, XP005942749 ISSN: 1051-0443 the whole document.

(Continued)

*Primary Examiner* — Michael Peffley

(57) ABSTRACT

A therapy planning and image guidance and navigation for an interventional procedure are combined in one system. The system includes: a radio frequency ablation therapy planning component (1) capable of creating an initial treatment plan, adjusting the treatment plan to take into account data received during a procedure and transferring a treatment plan to a navigation component, a navigation system component (2) to guide an ablation probe (6) and a feedback sub-system (3) for determining actual ablation probe positions/orientations and actual ablation size/shape via imaging (4) and/or tracking (5) systems, and enabling exchange of information between the planning component and the navigation component. By combining and integrating procedure planning and navigation, and by providing feedback from the navigation component back to the planning component about actual electrode position and orientation and ablation volume, complex procedures can be carried out more accurately, efficiently, and potentially with better clinical outcomes.

20 Claims, 2 Drawing Sheets

(51) Int. Cl.
*A61B 18/12* (2006.01)
*A61B 19/00* (2006.01)
*A61N 7/02* (2006.01)

(52) U.S. Cl.
CPC ......... *A61B18/1477* (2013.01); *A61B 19/5244* (2013.01); *A61B 2018/1425* (2013.01); *A61B 2019/504* (2013.01); *A61B 2019/507* (2013.01); *A61B 2019/5251* (2013.01); *A61B 2019/5276* (2013.01); *A61N 7/02* (2013.01)

(56) References Cited

U.S. PATENT DOCUMENTS

| | | | |
|---|---|---|---|
| 6,019,724 | A | 2/2000 | Gronningsaeter et al. |
| 6,241,725 | B1 * | 6/2001 | Cosman ................ 606/41 |
| 6,428,537 | B1 * | 8/2002 | Swanson et al. ............ 606/41 |
| 6,451,015 | B1 * | 9/2002 | Rittman et al. ............ 606/34 |
| 6,478,793 | B1 * | 11/2002 | Cosman et al. ............ 606/34 |
| 2003/0078490 | A1 | 4/2003 | Damasco et al. |
| 2004/0097805 | A1 * | 5/2004 | Verard et al. ............ 600/428 |
| 2005/0085718 | A1 | 4/2005 | Shahidi |
| 2006/0247608 | A1 | 11/2006 | Hahn et al. |
| 2007/0049827 | A1 | 3/2007 | Donaldson |
| 2007/0118100 | A1 | 5/2007 | Mahesh et al. |
| 2007/0230757 | A1 | 10/2007 | Trachtenberg et al. |
| 2008/0033417 | A1 | 2/2008 | Nields et al. |
| 2008/0033419 | A1 | 2/2008 | Nields et al. |
| 2008/0033420 | A1 | 2/2008 | Nields et al. |
| 2008/0065061 | A1 | 3/2008 | Viswanathan |
| 2009/0227997 | A1 | 9/2009 | Wang et al. |
| 2010/0036378 | A1 | 2/2010 | Savery et al. |
| 2010/0168571 | A1 | 7/2010 | Savery et al. |

OTHER PUBLICATIONS

Baegert, C. et al. "Trajectory optimization for the planning of percutaneous radiofrequency ablation of hepatic tumors". Computer Aided Surgery 2007; 12:82-90.

Villard, C. et al. "Radiofrequency ablation of hepatic tumors: simulation, planning, and contribution of virtual reality and haptics". Comput Methods Biomech Biomed Engin 2005; 8:215-227.

Butz, T. et al. "Pre- and Intra-operative Planning and Simulation of Percutaneous Tumor Ablation". Lecture Notes in Computer Science, MICCAI 2000; 1935:317-326.

Khajanchee Y.S. et al. "A mathematical model for preoperative planning of radiofrequency ablation of hepatic tumors". Surg Endosc 2004; 18:696-701.

Krucker, J. et al. "Electromagnetic Tracking for Thermal Ablation and Biopsy Guidance: Clinical Evaluation of Spatial Accuracy". Journal of Vascular and Interventional Radiology 2007; 18:1141-1150.

Banovac, F. et al. "An image-guided system for optimized volumetric treatment planning and execution for radiofrequency ablation of liver tumors". In:Int J Cars. Berlin, Germany: Springer, 2007; S146-S147.

* cited by examiner

FEEDBACK SYSTEM FOR INTEGRATING INTERVENTIONAL PLANNING AND NAVIGATION

The United States Government may have certain rights in this invention pursuant to Cooperative Research and Development Agreement No. NCI-NIHCC-01864 between the United States Public Health Service and Philips Medical Systems (Cleveland), Inc. and Philips Electronics North America Corporation.

The present application relates to the therapeutic arts, in particular to systems and methods for integrating interventional planning and navigation, particularly for tissue ablation therapy.

Interventional procedures such as radiofrequency ablation (RFA) have been performed in increasing numbers in recent years as an alternative to more invasive surgical procedures. During RFA, an electrode with an un-insulated tip is inserted into a tumor or lesion to be ablated under ultrasound, CT or MRI guidance. When the electrode is placed, a radiofrequency current is applied to the tip which creates tissue heating and cell death when tissue temperatures exceed 60° Celsius. In order to destroy tumors that are larger than the volume around the needle tip that is heated and destroyed in a single ablation, the needle tip needs to be repeatedly repositioned to ablate different parts of the tumor, partly overlapping with one another. This process needs to be repeated until the entire tumor is "covered" by the plurality of ablations, also referred to as the "composite ablation."

There are two main difficulties associated with this process, which explain in part the relatively poor outcomes for ablations of large (>3 cm) tumors:
1. The optimal three-dimensional (3D) positions of all individual ablations are difficult to plan manually/without computer assistance, where "optimal" refers to the use of the lowest number of overlapping ablations that fully covers the tumor plus surrounding safety margin (tumor+margin are also known as the Planned Target Volume, or PTV), and, for a given number of ablations, the placement of ablations that destroys the smallest volume of healthy, non-PTV tissue.
2. Even if the optimal positions of all individual ablations for one treatment (the Ablation Plan) were known, it is difficult to accurately execute a treatment plan, i.e. physically position the electrode in the desired locations, with conventional US, CT or MR guidance alone. Because of the uncertainty about the actual probe position during one ablation, this can affect the necessary placement of subsequent ablations.

Additional problems arise because it is difficult to obtain patient-specific information about expected actual ablation sizes in order to create an optimal patient-specific plan, and so plans must use estimated ablation sizes which may not be accurate. Further, a slowdown of the procedure workflow is caused when trying to work with non-integrated planning and navigation feedback systems.

RFA planning systems have been developed to address the first problem outlined above, but the systems are stand-alone and primarily used to visualize the desired set of ablations. Also, navigation systems have been developed to improve conventional image guidance by, for example, referencing the electrode position directly to the 3D coordinates of a pre-acquired medical image (e.g. a CT scan). However, these navigation systems exist independently of planning systems and are thus not useful in executing the procedure plan.

Navigation systems have been suggested that assist in guiding an ablation electrode to a target location inside the human body, but the known systems are not integrated with RFA planning.

US Patent Application Publication No. 2007/0230757 to Trachtenberg et al. uses image processing to identify a target area for treatment of malignant prostate tissue, and to monitor the energy delivery during treatment. This publication does not deal with solving problems related to coverage of the tumor, nor in planning for treatment.

US Patent Application Publication No. 2008/0033417 to Nields et al. relates to a thermal ablation system in which a controller compares actual temperature changes in the tissue during thermal ablation to a thermal ablation plan. No indication is given as to how applicator position is determined, and the thermal changes are not related to position feedback for revising the ablation plan.

The Summary is provided to comply with U.S. rule 37 C.F.R. §1.73, requiring a summary of the invention briefly indicating the nature and substance of the invention. It is submitted with the understanding that it will not be used to interpret or limit the scope or meaning of the claims.

In accordance with one aspect of the exemplary embodiments, a therapy planning and image guidance and navigation for an interventional procedure are combined in one system. The system includes an ablation probe for treating a tissue of interest with at least one of RF ablation, cryo-ablation, microwave ablation, ultrasound ablation, and other thermal or non-thermal ablation. A planning component is included for calculating a three-dimensional treatment plan including a plurality of desired ablation probe placement positions and orientations and a plurality of estimated ablation volumes to achieve a desired composite ablation volume that will treat the entire planned target volume (PTV). A navigation component is provided for spatially tracking the treatment probe and/or imaging device and providing treatment instructions to an operator based on the three-dimensional treatment plan. An imaging component for obtaining planning and treatment images of the tissue to be treated is also provided. The system further includes a feedback component for determining actual probe position and orientation using the navigation component or imaging component, and for determining actual ablation volume based on treatment images provided by the imaging component, and feeding the actual probe position/orientation and actual ablation volume during treatment to the planning component. The planning component calculates a treatment iteration based on the executed treatment plan, the actual probe position/orientation and actual ablation volume, the treatment iteration resulting in at least one of a desired next probe position/orientation and a desired next ablation volume. The navigation component provides revised treatment instructions to the operator based on the treatment iteration until treatment is completed according to the desired planned target volume.

Another aspect of the exemplary embodiments relates to a method of ablation therapy of tissue. The method includes calculating a three-dimensional treatment plan for a tissue of interest including a plurality of desired ablation probe placement positions and orientations and a plurality of estimated ablation volumes to achieve a desired composite ablation volume that will treat the entire planned target volume (PTV). The method further includes providing treatment instructions to an operator based on the three-dimensional treatment plan, and treating the tissue of interest with at least one of RF ablation, cryo-ablation, microwave ablation, ultrasound ablation, and other thermal or non-thermal ablation. Planning and treatment images of the tissue to be treated are obtained, and actual probe position/orientation and actual ablation volume based on the treatment images are determined. A treatment iteration is calculated based on the treatment plan, the actual probe position/orientation and actual ablation volume, the treatment iteration resulting in at least one of a desired next probe position and a desired next ablation volume. The method further includes providing revised treatment instructions to the operator based on the treatment iteration and continuing iterative treatment until treatment is completed according to the desired planned target volume.

In another aspect of the exemplary arrangements of the invention, a control system for ablation treatment of tissue includes a planning component for calculating a three-dimensional treatment plan including a plurality of desired ablation probe placement positions and orientations and a plurality of estimated ablation volumes to achieve a desired planned target volume that will treat an entire tissue volume of interest. An imaging component for obtaining treatment images of the tissue to be treated is also included, along with a feedback component for calculating actual probe position/orientation and actual ablation volume based on treatment images provided by the imaging component, and feeding the actual probe position/orientation and actual ablation volume during treatment to the planning component. The planning component maps the actual probe location and actual ablation volume to the three-dimensional plan and calculates a treatment iteration based on the treatment plan, the actual probe position/orientation and actual ablation volume, the treatment iteration resulting in at least one of a desired next probe position/orientation and a desired next ablation volume.

Many interventional procedures such as radiofrequency ablation (RFA) are commonly carried out without dedicated or computer-assisted planning, and with only basic image guidance. By combining and integrating procedure planning and navigation, and by providing feedback from the navigation component back to the planning component about actual electrode position and ablation size/shape, complex procedures can be carried out more accurately, efficiently, and potentially with better clinical outcomes. Both procedure planning and advanced image guidance and navigation can improve the accuracy of procedure execution, yielding several advantages such as improved patient outcomes, reduced use of ionizing radiation, and reduced cost.

The above-described and other features and advantages of the present disclosure will be appreciated and understood by those skilled in the art from the following detailed description, drawings, and appended claims.

The exemplary embodiments of the present disclosure are described with respect to ablative therapy of a human. It should be understood by one of ordinary skill in the art that the exemplary embodiments of the present disclosure can be applied to other types of ablative therapy and other portions of the body, whether human or animal. The use of the method and system of the exemplary embodiments of the present disclosure can be adapted for application to other types of applicators.

Figure 1:
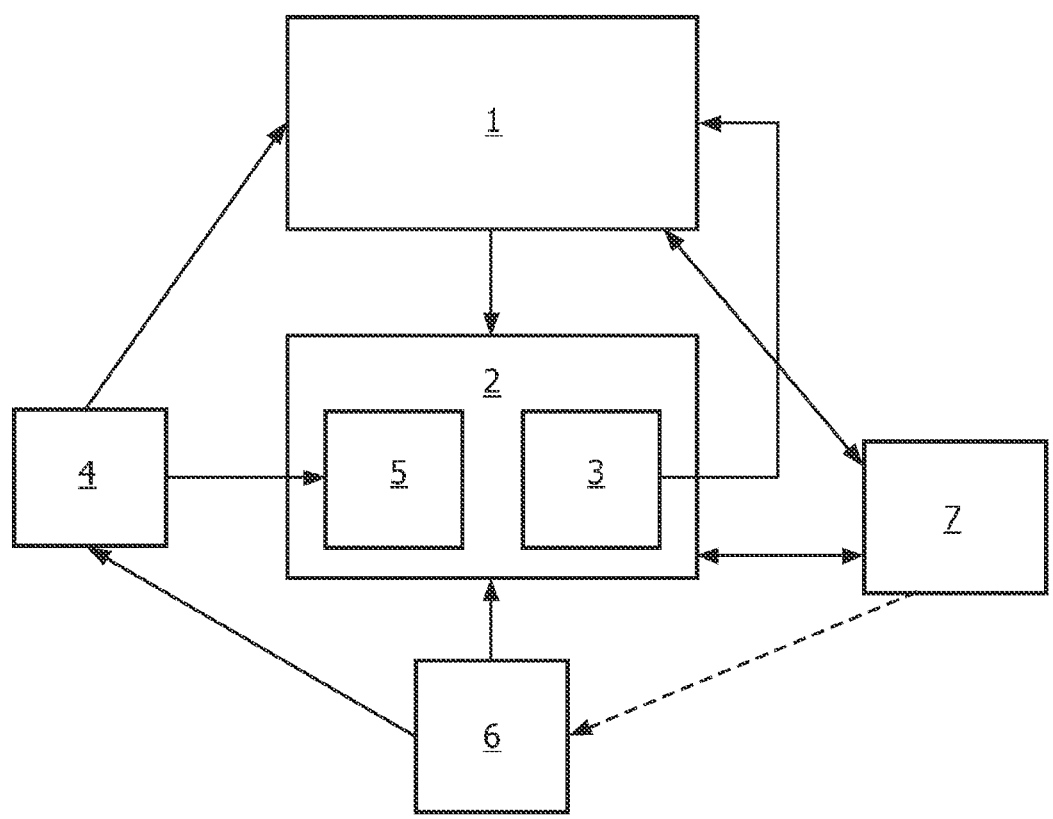
FIG. 1 shows components of the present invention.

Referring to FIG. 1, a feedback system for integrating interventional planning and navigation of ablation treatment can include a planning component (1) for planning radiofrequency ablation (RFA) therapy (or other ablative therapy including, but not limited to, cryo-ablation, microwave ablation, ultrasound ablation, or other thermal or non-thermal ablation), and which is capable of creating an initial treatment plan, and adjusting the treatment plan to take into account data received during a procedure and transferring the treatment plan to a navigation component. The system includes a navigation system component (2) to guide an ablation probe (6) to target locations via a graphical user interface (7); and a feedback sub-system (3) for determining actual ablation probe positions/orientations and actual ablation size/shape via imaging (4) and/or tracking (5) systems, and enabling exchange of information between the navigation component (2) and the planning component (1). By combining and integrating procedure planning and navigation, and by providing feedback from the navigation component (2) back to the planning component (1) about actual ablation probe position and actual ablation size, complex procedures can be carried out more accurately, efficiently, and potentially with better clinical outcomes.

The planning system component (1) can allow computation of a composite ablation consisting of a plurality of optimal individual ablation positions/orientations based on input of a desired planned target volume (PTV) to be covered, and estimated or known individual ablation sizes. The desired composite ablation volume is comprised of a plurality of ablations that together will treat the entire PTV. The planning system component (1) utilizes image data acquired from the imaging component (4) of the system. Inputs to the planning component (1) can include a baseline image of the tissue to be treated from the imaging component (4), PTV segmentation, desired individual ablation shape and size, and desired skin entry point(s) selected by the treating physician. The planning system component (1) can calculate an initial plan for treatment, which is a 3-D mapping of the optimal number of ablations that will cover the PTV. The planning system component also has the capability to use feedback about the actual ablation positions or sizes, or actual tumor location relative to the ablation probe, to update or refine the plan iteratively. A plan includes the optimal number of ablations that will completely treat/ablate the PTV, the 3D location of each of those individual ablations, and the orientation of each of those individual ablations. The 3D location of an ablation is referred to as a planned target location in the navigation component (2). The planning system component (1) can output the plan information to a graphical user interface (GUI) (7) for use by a physician operator.

The navigation system component (2) with monitoring and feedback capability, which provides visual guidance via a GUI (7) to assist in delivering an ablation probe (6) to any of the planned target locations can determine the actual ablation probe position (via the imaging component (4) or tracking sub-system (5)), the actual individual ablation size/shape (via the imaging component (4) when using e.g. ultrasound elastography), and the actual tumor location relative to the ablation probe (via imaging). Imaging means (4) may include handheld imaging devices, static imaging devices, etc. Other factors that may affect the execution of the procedure such as blood flow/perfusion near the ablation site, which can serve as a "heat sink" and thereby reduce the size of or deform the individual ablation shape can also be monitored. The navigation system component (2) registers the baseline image with the ablation probe and treatment images using the tracking system (5), and then provides guidance to the physician for guiding the needle to any of the target locations for ablation.

The feedback component sub-system (3) can allow the navigation system component (2) to provide information about the ablation probe position and orientation, ablation size/shape, local perfusion, or other information obtained during the execution of one ablation to the planning system component. The feedback component (3) allows the planning system component (1) to receive any such information relevant for procedure planning from the navigation system component (2), to use it to update and refine the treatment plan iteratively, and to send the updated plan back to the navigation system component to guide subsequent ablations in an iterative process.

Figure 2:
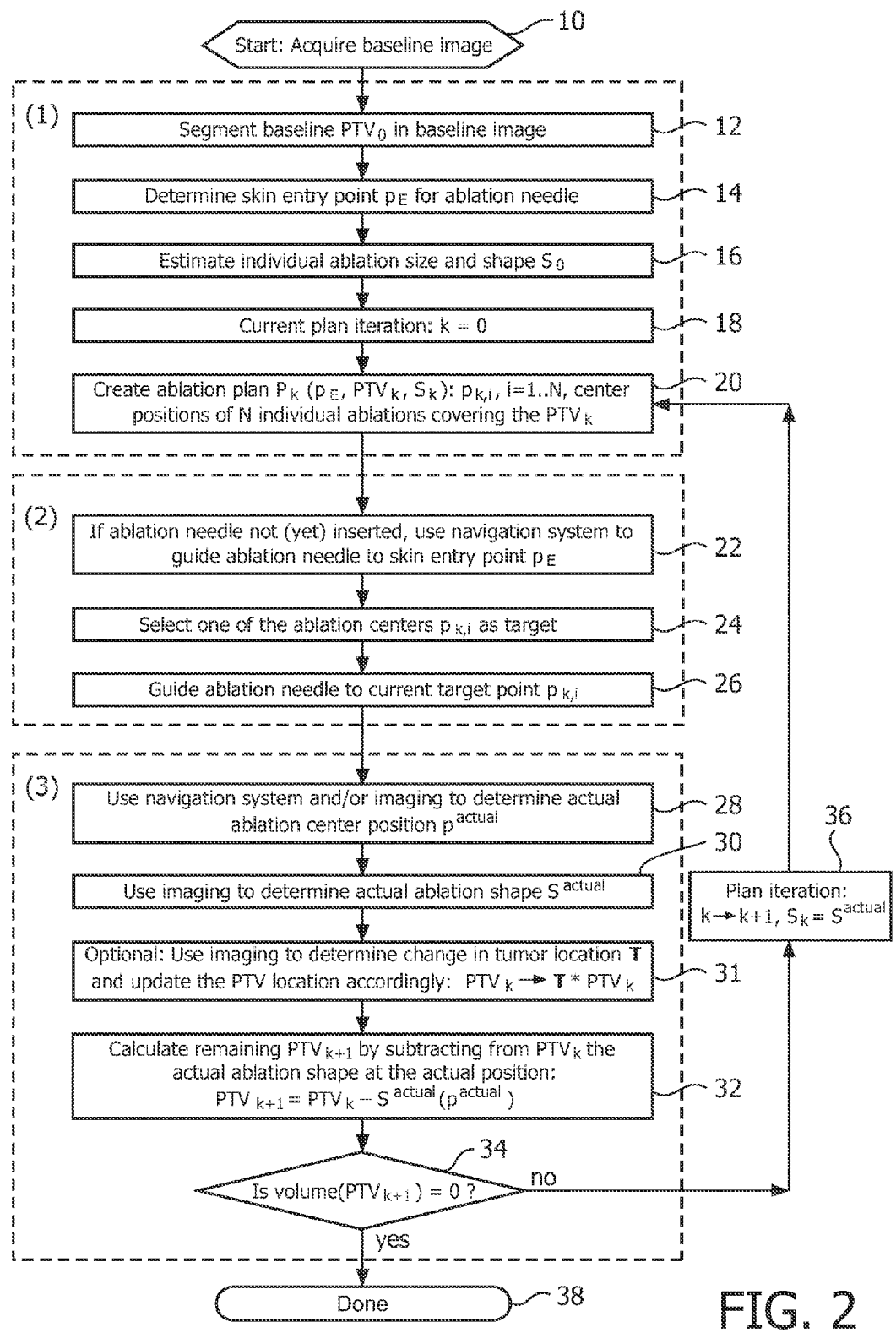
FIG. 2 is a flowchart of the ablation planning and navigation system with feedback.

Referring to FIG. 2, a detailed flowchart of the ablation planning and navigation method with feedback is illustrated. The method starts at step 10 with acquisition of baseline images prior to treatment.

The planning system component (1) allows determination of optimal ablation positions to treat an arbitrarily sized or shaped tumor with multiple, overlapping ablations, such as by RFA ablation. This component requires input and visualization of an image data set (the "baseline image") and the ability to segment a tumor or PTV, or to import the segmentation from elsewhere. The planning system component segments the baseline $PTV_0$ in the baseline image at step 12. The planning system component can also determine the skin entry point $p_E$ for the ablation needle at step 14, or this can be entered into the system after having been determined by a physician.

The planning system component at a minimum also requires as an input the estimated shape and size $S_0$ of an individual ablation (step 16). Based on these inputs, the component can set the current (initial) iteration as k=0 (step 18), and allows creation of a treatment plan either manually or automatically (step 20). For manual plan creation, the component visualizes the PTV and provides a graphical user interface (GUI) for the user to manually place one or more ablations (each modeled by an estimated shape and size $S_0$) to cover the PTV. For automatic plan creation, the planning system component (1) determines an optimal set of ablation positions $P_k$, based on the assumed/estimated individual ablation size and shape:

$$P_k(p_E, PTV_k, S_k): p_{k,i}, i=1 \ldots N_k$$

to provide the center positions $p_{k,i}$ of $N_k$ individual ablations covering the $PTV_k$ where k is the iteration index. The value of $N_k$ is not a constant for all iterations but will usually decrease as the iterative treatment proceeds from step k=0 through step k=1, 2 or more.

If the ablation probe needle has not (yet) been inserted, the physician operator can use the navigation system to guide the ablation needle to the skin entry point $p_E$ (step 22). The operator can then select one of the ablation centers $p_{k,i}$ as the target (step 24). The navigation component (2) and feedback component sub-system (3) comprise a system to guide the ablation electrode insertion to the specified target location $p_{k,i}$ inside the human body (step 26). One suitable guiding system is the commercially available Traxtal PercuNav™ system, which uses electromagnetic tracking to register the electrode position with a medical image of the patient. The navigation component (2) uses the same "baseline image" as the planning component (1), or can use a different image that is spatially registered with the baseline image.

The navigation system component (2) has the ability to import an entire treatment plan from the planning component (1), consisting of multiple individual ablation locations, and potentially individual skin entry points for each of the ablation electrode placements. The navigation component will visualize the treatment plan by rendering the segmented PTV and the planned ablation locations in 3D, and will provide a GUI for the physician to select which of the planned target locations are to be executed next. For each ablation, the navigation system component (2) provides guidance of the electrode (6) to the planned skin entry point first, and from there to the planned ablation position. In case the physician selects a next target location that is near to the current ablation target, the system can provide guidance of the ablation probe electrode (6) directly to the next target without requiring complete retraction of the needle.

Furthermore, the navigation system component (2) also contains a feedback sub-system (3) to obtain feedback about the actual electrode position/orientation during an ablation, and about the actual ablation size/shape and tumor location/orientation. The feedback sub-system (3) has the ability to provide that feedback to the planning component (1) for iterative refinement of the plan for subsequent ablations. The feedback subsystem (3) uses the imaging system (4) and/or tracking system (5) to determine the actual ablation center position $p^{actual}$ (step 28).

The position feedback $p^{actual}$ can be obtained in any suitable way, such as the following:

1. For procedures performed on a CT or MRI scanner (independent of the use of a spatial tracking system), a confirmation CT or MRI image can be obtained with the electrode in position for an ablation, and the scan transferred to the navigation component. The confirmation scan is registered with and superimposed on the baseline navigation image. The electrode tip will be identified in the confirmation scan, and a GUI allows the user to transfer that position to the baseline image and send it to the planning component.
2. For procedures performed with spatial tracking of the ablation electrode tip (e.g. using the Traxtal PercuNav™ system), a GUI is provided for the user to initiate the conversion of the electrode's tracking coordinates into baseline image coordinates using the navigation component's registration transformation, and to send the position to the planning component.

Optionally, when the position feedback is obtained with both imaging and tracking, the combined information can be used to update/improve the coordinate registration between the image and tracking systems, thus allowing more accurate navigation in subsequent iterative steps.

Ablation size/shape feedback to determine the actual ablation shape $S^{actual}$ (step 30) can be obtained in the following way: A three-dimensional (3D) medical image of the ablation area (e.g. CT, MRI, ultrasound) that provides adequate grayscale-contrast to allow delineation of the ablation zone can be obtained during or shortly after an ablation, and the image transferred to the navigation component. A GUI can be provided for the user to measure the size/shape of the ablation in one or several dimensions, based on the visible ablation contrast in the image. Alternatively, an automated or semi-automated algorithm can extract the shape of the ablation with limited or no user input The size/shape information is transferred to the planning component in order to update the plan for the remaining ablations with the measured ablation size/shape as the new ablation size/shape estimate.

Optionally, the feedback component can be use to detect any changes in the tumor location e.g. due to patient motion including respiratory motion, by comparing the initial tumor location in the baseline image with the actual tumor location in the most recent image obtained by the imaging component (4). The location of the PTV is then updated according to the transformation T describing the change in tumor location: (step 31)

$$PTV_k \rightarrow T^* PTV_k$$

The planning component (1) receives the feedback information and updates the plan for the remainder of the procedure if the measured position or ablation size/shape deviate from the planned/assumed position and size/shape. In particular, the planning component can subtract the measured ablation size/shape at the measured ablation position from the initially segmented PTV$_k$, and compute a new plan for the remaining PTV$_{k+1}$ (step 32):

$$PTV_{k+1} = PTV_k - S^{actual}(p^{actual})$$

The iterative process will continue until the entire PTV volume is ablated. This can be determined by computing the volume (PTV$_{k+1}$)=0 (step 34). If the PTV volume is not zero, i.e. there are a finite number of unablated voxels in the PTV, the plan iteration is followed so that k→k+1, S$_k$=S$^{actual}$ (step 36). If the PTV volume is zero, such that no non-ablated PTV remains, the treatment procedure ends at step 38. In specific instances, the physician may exercise his/her judgment to terminate the iterative process in case the remaining volume of the PTV is relatively small and visualization of this small PTV in the GUI interface of the planning component provides confidence in making that decision.

It should be appreciated that the invention can be used with RFA ablation, cryo-ablation, microwave ablation, ultrasound ablation, or other thermal or non-thermal ablation, and is not intended to be limited in this regard.

The invention, including the steps of the methodologies described above, can be realized in hardware, software, or a combination of hardware and software. The invention can be realized in a centralized fashion in one computer system, or in a distributed fashion where different elements are spread across several interconnected computer systems. Any kind of computer system or other apparatus adapted for carrying out the methods described herein is suited. A typical combination of hardware and software can be a general purpose computer system with a computer program that, when being loaded and executed, controls the computer system such that it carries out the methods described herein.

The invention, including the steps of the methodologies described above, can be embedded in a computer program product. The computer program product can comprise a computer-readable storage medium in which is embedded a computer program comprising computer-executable code for directing a computing device or computer-based system to perform the various procedures, processes and methods described herein. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

The illustrations of embodiments described herein are intended to provide a general understanding of the structure of various embodiments, and they are not intended to serve as a complete description of all the elements and features of apparatus and systems that might make use of the structures described herein. Many other embodiments will be apparent to those of skill in the art upon reviewing the above description. Other embodiments may be utilized and derived therefrom, such that structural and logical substitutions and changes may be made without departing from the scope of this disclosure. Figures are also merely representational and may not be drawn to scale. Certain proportions thereof may be exaggerated, while others may be minimized. Accordingly, the specification and drawings are to be regarded in an illustrative rather than a restrictive sense.

Thus, although specific embodiments have been illustrated and described herein, it should be appreciated that any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description. Therefore, it is intended that the disclosure not be limited to the particular embodiment(s) disclosed as the best mode contemplated for carrying out this invention, but that the invention will include all embodiments falling within the scope of the appended claims.

The Abstract of the Disclosure is provided to comply with U.S. rule 37 C.F.R. §1.72(b), requiring an abstract that will allow the reader to quickly ascertain the nature of the technical disclosure. It is submitted with the understanding that it will not be used to interpret or limit the scope or meaning of the claims.

What is claimed is:

1. A system for ablation treatment of tissue, comprising:
   an ablation probe (6) for treating a tissue of interest with at least one of RF ablation, cryo-ablation, microwave ablation, ultrasound ablation, or other thermal or non-thermal ablation;
   a planning component (1) for calculating a three-dimensional treatment plan including a plurality of desired ablation probe placement positions and orientations and a plurality of estimated ablation volumes to achieve a composite ablation volume that will treat an entire planned target volume (PTV);
   a navigation component (2) comprising a tracking system (5) for spatially tracking at least one of the ablation probe and an imaging device and providing treatment instructions to an operator based on the three-dimensional treatment plan;
   an imaging system (4) for obtaining planning and treatment images of the tissue to be treated; and
   a feedback component (3) for determining actual probe position and orientation using the navigation component or imaging component, and for determining actual ablation volume based on treatment images provided by the imaging component (4), and feeding the actual probe position and orientation and actual ablation volume during treatment to the planning component (1),
   wherein the planning component (1) determines a treatment iteration based on the treatment plan, the actual probe position and orientation and actual ablation volume, the treatment iteration including at least one of a desired next probe position and orientation and a desired next ablation volume,
   wherein the navigation component (2) provides revised treatment instructions to the operator based on the treatment iteration until treatment is completed according to the desired planned target volume,
   characterized in the feedback component (3) being configured to obtain information including imaging feedback and tracking feedback about the actual probe location, and provide the information including both the imaging feedback and tracking feedback to the planning component (1) to update the three-dimensional treatment plan,
   wherein the planning component (1) receives the information and updates the plan by subtracting a measured ablation size and shape at a measured ablation position from an initially segmented planned target volume, and computes a new plan for a remaining part of the planned target volume.

2. The system according to claim 1, wherein the imaging component (4) provides at least one of ultrasound, CT, MR imaging, ultrasound elastography, and Doppler ultrasound, and wherein the navigation component provides at least one of spatial tracking coordinates of the ablation probe and imaging, based on at least one of electromagnetic (EMP), optical, acoustic, and magnetic tracking sensors.

3. The system according to claim 1, further comprising a user interface for displaying the treatment iteration instructions from the navigation component (2) for access by a human operator.

4. The system according to claim 1, wherein the feedback component (3) further calculates at least one of local micro-vascular perfusion and macro-vascular blood flow parameters near the ablation site and provides the information to the planning component (1) for incorporation into the treatment iteration.

5. The system according to claim 1, wherein the feedback component (3) registers treatment images with planning images to calculate at least one of the actual probe position and orientation and tumor position and orientation, and uses the information to update the three-dimensional treatment plan; and
wherein the planning component (1) utilizes center positions of individual ablations for calculating the three-dimensional treatment plan.

6. The system according to claim 1, wherein the feedback component (3) obtains imaging feedback and tracking feedback about actual probe location, and uses the information to update and improve registration between the imaging system and the tracking system.

7. A method of ablation therapy of tissue, comprising:
calculating, in a planning component, a three-dimensional treatment plan (20) for a tissue volume of interest including a plurality of desired ablation probe placement positions and orientations and a plurality of estimated ablation volumes to achieve a desired planned target volume that will treat the entire tissue volume of interest;
providing treatment instructions (14) to an operator based on the three-dimensional treatment plan;
treating the tissue volume of interest with at least one of RF ablation, cryo-ablation, microwave ablation, ultrasound ablation, and other thermal or non-thermal ablation;
obtaining planning (10) images and treatment images, from an imaging system, of the tissue volume to be treated;
determining, in a feedback component, actual probe position and orientation and actual ablation volume (30) based on the treatment images; and
calculating a treatment iteration (32), in the planning component, based on the treatment plan, the actual probe position and orientation and actual ablation volume, the treatment iteration including at least one of a desired next probe position and a desired next ablation volume, and
providing revised treatment instructions to the operator based on the treatment iteration and continuing iterative treatment until treatment is completed according to the desired planned target volume, wherein
the planning component (1) receives the information and updates the plan by subtracting a measured ablation size and shape at a measured ablation position from an initially segmented planned target volume, and computes a new plan for a remaining part of the planned target volume.

8. The method according to claim 7, wherein the imaging component provides at least one of ultrasound, CT, MR imaging, ultrasound elastography, and Doppler ultrasound, and wherein the navigation component provides at least one of spatial tracking coordinates of the therapy probe and imaging based on at least one of electromagnetic (EM), optical, acoustic, and magnetic sensors.

9. The method according to claim 7, wherein the treatment is carried out by a human operator accessing at least one of the treatment plan and the treatment iteration instruction from a user interface.

10. The method according to claim 7, wherein at least one of local micro-vascular perfusion and macro-vascular blood flow parameters near the ablation site are calculated and this information is incorporated into the treatment iteration.

11. The method according to claim 7, wherein the treatment images are registered with planning images to calculate at least one of the actual probe position and orientation and tumor position and orientation, and to use the information to update the three dimensional treatment plan, and
wherein the planning component (1) utilizes center positions of individual ablations for calculating the three-dimensional treatment plan.

12. The method according to claim 7, wherein treatment images showing the actual ablation probe location and tracking data representing the actual probe position are used to update the registration between the imaging system and the tracking system.

13. A control system for ablation treatment of tissue, comprising:
a planning component (1) for calculating a three-dimensional treatment plan including a plurality of desired ablation probe placement positions and orientations and a plurality of estimated ablation volumes to achieve a desired planning target volume that will treat an entire tissue volume of interest;
a navigation component (2) comprising a tracking system (5) for spatially tracking at least one of the ablation probe and an imaging device;
an imaging system (4) for obtaining treatment images of the tissue to be treated; and
a feedback component (3) for calculating actual probe position and orientation of a probe and actual ablation volume based on treatment images provided by the imaging component, and feeding the actual probe position and orientation and actual ablation volume during treatment to the planning component,
wherein the planning component (1) maps the actual probe location and actual ablation volume to the three-dimensional plan and calculates a treatment iteration based on the treatment plan, the actual probe position and orientation and actual ablation volume, the treatment iteration including at least one of a desired next probe position and orientation and a desired next ablation volume,
characterized in that the feedback component (3) obtains information including imaging feedback and tracking feedback about the actual probe location, and provides the information including both the imaging feedback and tracking feedback to the planning system to update the three-dimensional treatment plan, and
wherein the planning component (1) receives the information and updates the plan by subtracting a measured ablation size and shape at a measured ablation position from an initially segmented planned target volume, and computes a new plan for a remaining part of the planned target volume, and
wherein the planning component (1) receives the information and updates the plan by subtracting a measured ablation size and shape at a measured ablation position from an initially segmented planned target volume, and computes a new plan for a remaining part of the planned target volume.

14. The control system according to claim 13, wherein the imaging component (4) provides at least one of ultrasound, CT, MR imaging, ultrasound elastography, and Doppler ultrasound, and wherein the navigation component provides at least one of electromagnetic (EM), optical, acoustic, and magnetic sensors.

15. The control system according to claim 13, wherein the control system delivers the next treatment ablation according to the calculated treatment iteration by at least one of moving the ablation probe to the desired next probe position and ablating the next desired ablation volume.

16. The control system according to claim 13, wherein the feedback component (3) further calculates at least one local micro-vascular perfusion and macro-vascular blood flow parameters near the ablation site and provides this information to the planning component for incorporation into the treatment iteration.

17. The control system according to claim 13, wherein the feedback component (3) registers treatment images with planning images to calculate at least one of the actual probe position and orientation and tumor position and orientation, and uses the information to update the three-dimensional treatment plan; and wherein the planning component (1) utilizes center positions of individual ablations for calculating the three-dimensional treatment plan.

18. The control system according to claim 13, wherein the feedback component (3) obtains imaging feedback and tracking feedback about the actual probe location and uses the information to improve registration between the imaging system (4) and tracking system (5).

19. The control system according to claim 14, wherein the imaging component (4) utilizes a contrast medium.

20. The control system according to claim 13, wherein the planning component (1) utilizes center positions of individual ablations for calculating the three-dimensional treatment plan.

* * * * *